United States Patent [19]

Baehr

[11] 4,157,718
[45] Jun. 12, 1979

[54] INTRA-OCULAR PRESSURE NORMALIZATION TECHNIQUE AND EQUIPMENT

[75] Inventor: Edward F. Baehr, Berea, Ohio

[73] Assignee: The United States of America as represented by the Administrator of the National Aeronautics and Space Administration, Washington, D.C.

[21] Appl. No.: 829,318

[22] Filed: Aug. 31, 1977

[51] Int. Cl.² .......................... A61M 1/00; A61M 5/14
[52] U.S. Cl. ................................................. 128/276
[58] Field of Search .................... 128/2.05 G, 2.05 D, 128/276, 2 T, 213, 215, 216, 227, 172, 350 R, 350 V

[56] References Cited

U.S. PATENT DOCUMENTS

| 3,185,153 | 5/1965 | Leucci | 128/DIG. 13 |
| 3,572,319 | 3/1971 | Bittner et al. | 128/213 |
| 3,931,818 | 1/1976 | Goldowsky | 128/227 |
| 4,078,563 | 3/1978 | Tuseth | 128/227 |
| 4,084,612 | 4/1978 | Baehr | 137/484.2 |

Primary Examiner—Robert W. Michell
Assistant Examiner—J. Kruter

Attorney, Agent, or Firm—Norman T. Musial; John R. Manning; James A. Mackin

[57] ABSTRACT

There is disclosed a method and apparatus for safely reducing abnormally high intra-ocular pressure in an eye during a predetermined time interval. This allows maintenance of normal intraocular pressure during glaucoma surgery. According to the invention, a pressure regulator of the spring-biassed diaphragm type is provided with additional bias by a column of liquid. The height of the column of liquid is selected such that the pressure at a hypodermic needle connected to the output of the pressure regulator is equal to the measured pressure of the eye. The hypodermic needle can then be safely inserted into the anterior chamber of the eye. Liquid is then bled out of the column to reduce the bias on the diaphragm of the pressure regulator and, consequently, the output pressure of the regulator. This lowering pressure of the regulator also occurs in the eye by means of a small second bleed path provided between the pressure regulator and the hypodermic needle. Alternately, a second hypodermic needle may be inserted into the eye to provide a controlled leak-off path for excessive pressure and clouded fluid from the anterior chamber.

11 Claims, 2 Drawing Figures

INTRA-OCULAR PRESSURE NORMALIZATION TECHNIQUE AND EQUIPMENT

ORIGIN OF THE INVENTION

This invention was made by an employee of the U.S. Government and may be manufactured or used by or for the Government of the United States without the payment of any royalties thereon or therefor.

BACKGROUND OF THE INVENTION

1. Field of the Invention

The invention relates to ophthalmic surgery and is directed more particularly to a method and apparatus for reducing intraocular pressure prior to surgery and for maintaining normal pressure during surgery.

2. Prior Art

Glaucoma is a disease of the eye involving abnormally elevated intraocular pressure. Such pressure can cause irreparable damage to the eye and eventual blindness. In the event that surgery is required on the eye, the intraocular pressure must be reduced to a safe level. Any attempt to penetrate the eye surgically while the pressure is markedly elevated involves a high risk of structural damage to the eye. This damage is a result of rapid pressure loss.

In the past, prior to opthalmic surgery, intraocular pressure has been reduced by the administration of drugs or the use of other systemic means. Such procedures often require a time-period of several hours or more to obtain the desired reduction in intraocular pressure. Additionally, drugs may have undesirable side effects on some people and/or may be insufficiently effective on others.

OBJECTS AND SUMMARY OF THE INVENTION

It is an object of the invention to provide a method and apparatus for controllably and safely reducing intraocular pressure in an eye.

It is another object of the invention to provide a method and apparatus for controllably reducing the pressure in an eye to a predetermined safe value and then maintaining the pressure constant during a glaucoma surgery.

Still another object of the invention is to provide a method and apparatus for reducing and controlling the pressure of liquid supplied to an eye and for removing fluid from the eye at a controlled rate.

In summary, the invention provides a method and apparatus for controllably and safely reducing intraocular pressure in an eye by providing means for biasing a pressure regulator connected between a source of treatment fluid and a hypodermic needle to be inserted into the eye such that the pressure at the hypodermic needle is equal to that measured for the eye. After the needle is inserted into the eye, the bias is then reduced in a predetermined manner.

DESCRIPTION OF A PREFERRED EMBODIMENT

Figure 1:
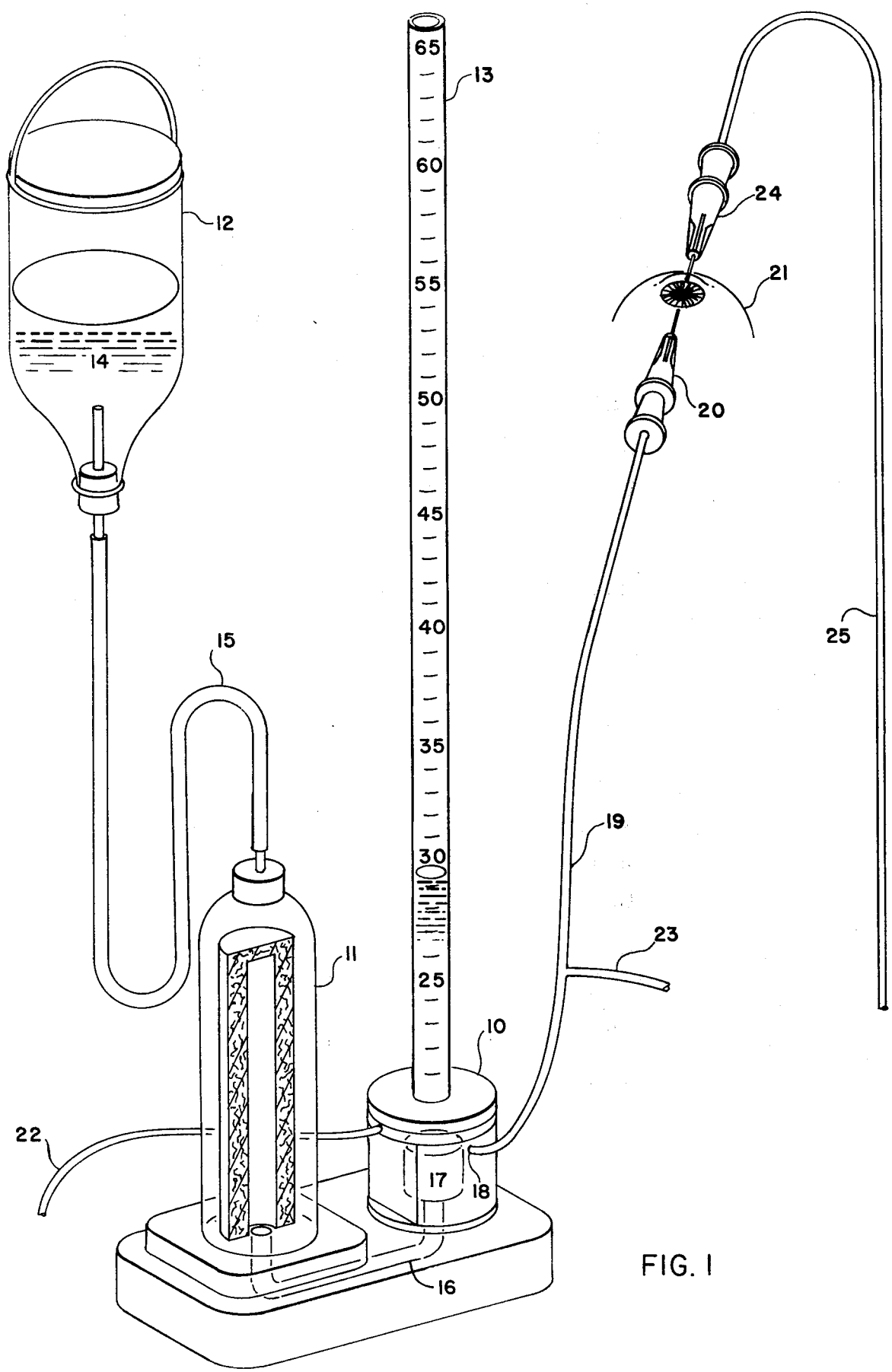
FIG. 1 is a pictorial diagram of apparatus utilized with the invention.

Referring now to FIG. 1 there is shown apparatus including a pressure regulator 10, a filter 11, a reservoir 12 and a vertical tube 13. A buffered saline solution 14 or treatment fluid flows from reservoir 12 through a conduit 15 and into filter 11. The fluid then flows out of the bottom of filter 11 and through a passageway 16 into an inlet chamber 17 of the pressure regulator 10. From inlet chamber 17 the fluid flows through a diaphragm controlled valve which is shown and described in FIG. 2 and out of an outlet port 18 through reflexible tube 19 and the hypodermic needle 20 into the interior chamber of an eye 21.

This will be explained more fully with regard to FIG. 2. A suitable fluid such as distilled water disposed in vertical tube 13 or standpipe increases the pressure of the fluid at outlet port 18. In order to gradually reduce the pressure at outlet port 18, the fluid level into 13 is reduced by bleeding-off fluid by means of a small length of tubing 22 which communicates with the bottom of tube 13. The diameter and length of tube 22 determine the bleed-off rate and, hence, tube 22 may be termed a bias bleed means.

Pressure regulator 10 is a one-way device in that fluid can flow only out of outlet 18. Consequently, when hypodermic needle 20 is inserted into the anterior chamber of eye 21, there is no flow-path for fluid which is to be removed from the eye. To provide such a path, a tube 23 communicates with tube 19 at some point between outlet 18 and hypodermic needle 20. The length and inside diameter of tube 23 must be selected to obtain the flow rate desired. Tube 23 thus serves as a pressure relief bleed means.

As an alternate pressure relief bleed path, particularly under conditions where the anterior chamber contains clouded fluid, a second hypodermic needle 24 may be inserted into the anterior chamber of the eye 21 and a tube 25 connected thereto carries away the fluid. As in the case of tube 22, the diameter and length of tube 25 determine the rate of removal of fluid from the anterior chamber of the eye. Tube 25 and hypodermic needle 24 comprise an irrigation bleed means.

Figure 2:
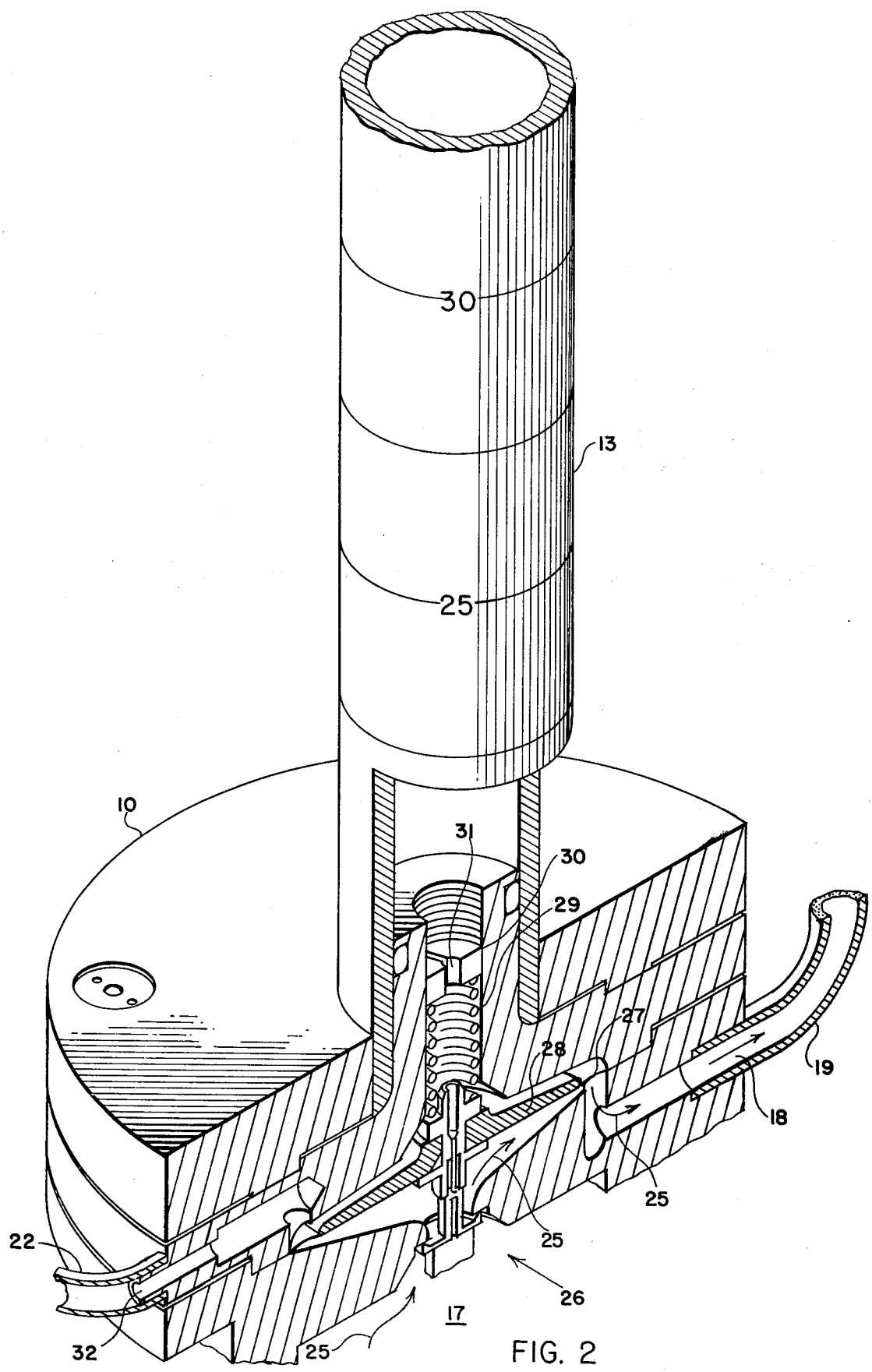
FIG. 2 is an oblique sectional view of the pressure regulator portion of FIG. 1.

Referring now to FIG. 2, there is shown an oblique cutaway view of the essential parts of pressure regulator 19. Parts corresponding to those of FIG. 1 are identified by like numerals. Pressure regulator 10 includes a valve 26, a diaphragm 27 supported on a backing plate 28, and a bias spring 29. Spring 29 exerts pressure against backing plate 28 to open valve 26. Fluid, as indicated by arrows 25, flows through the valve 26 against the underside of diaphragm 27 and through outlet port 18 into tube 19. The compression of spring 29 determines the pressure of the fluid at outlet port 18.

The pressure regulating components just described are well known in the prior art and are much like any standard diaphragm type pressure regulating device. However, a preferred pressure regulating device is the flow compensating pressure regulator disclosed and claimed in the copending application of Edward F. Baehr, Ser. No. 779,428, filed Mar. 21, 1977, now U.S. Pat. No. 4,084,612 and assigned to the assignee of the instant invention.

As shown in FIG. 2, an adjuster 30 is provided to change the compression of spring 29 so that the pressure at outlet port 18 may be adjusted to a desired value. An aperture 31 is provided in adjuster 30 so that fluid in vertical tube 13 may flow through the adjuster and past the spring 29 to the upper side of diaphragm 27 and through a bleed-off outlet port 32 into the tube 22. The pressure of the fluid adds to the bias of spring 29 to increase the pressure at outlet port 18. Thus, the height of the fluid in tube 13 can be adjusted such that the pressure at outlet 18 is equal to the measured intraocular pressure.

According to the inventive method, the intraocular pressure of an eye diseased by glaucoma, for example, is measured. A reservoir such as 12 containing a treatment of fluid 14 is provided and connected to a tube such as 15 and 19 to the hypodermic needle 20. The reservoir 12 is raised to a height such that the fluid pressure at the tip of hypodermic needle 20 is equal to that measured in the eye as, for example, 60 mm of mercury. Hypodermic needle 20 is then inserted into the anterior chamber of the eye and the reservoir is gradually lowered until the pressure at the tip of the hypodermic needle is approximately that of a normal eye, for example, 20 mm of mercury. At the same time, some pressure is bled off through a pressure relief bleed.

Preferably the fluid 14 is directed to a pressure regulator such as 10 which, after the initial pressure reduction, will maintain pressure constant at the hypodermic needle 20.

Utilizing the pressure regulator 10, the vertical tube 13 is filled with suitable fluid (distilled water) to a level such that pressure at hypodermic needle 20 is equal to that measured in the eye. After the hypodermic needle 20 is inserted into the anterior chamber of the eye, the bias bleed orifice, tube 22, bleeds-off fluid from the vertical tube 13 causing the pressure at hypodermic needle 20 to decrease from a high magnitude as, for example, 60 mm of mercury, to a normal level as, for example, 20 mm of mercury. The pressure relief bleed 23 relieves some of the pressure at outlet port 18 and, consequently, at hypodermic needle 20. After the pressure of the eye is reduced to a normal level, surgical procedures can be initiated.

Preferably, the flow compensating regulator of the previously identified copending patent application would be used. This pressure regulator includes means for controlling output pressure despite variations in the flow rate of fluid to the eye during operative procedures.

The range of dimensions of various components of the apparatus are given below in Table I with preferred dimensions in parenthesis.

TABLE I

|  | Length | Inside Diameter |
| --- | --- | --- |
| Standpipe 13 | 70–80cm (74 cm) | 1.27–2.5cm (2.24cm) |
|  | 27.5–31.5″(29″) | 0.5–1.0″(0.875″) |
| Tube 22 | 30–100cm (38cm) | 0.75mm–1.5mm (1.5mm) |
|  | 12″–39″(14.9″) | 0.031″–0.062″(0.062″) |
| Tube 23 | 50–200cm (100cm) | 0.75mm–1.5mm (0.75mm) |
|  | 18″–78″(39″) | 0.031″–0.062″(0.031″) |
| Tube 25 | 50–200mm (100cm) | 0.75mm–1.5mm (0.75mm) |

TABLE I-continued

| Length | Inside Diameter |
| --- | --- |
| 18″–78″(39″) | 0.031″–0.062″(0.031″) |

As shown in FIG. 1, standpipe 13 is calibrated to indicate actual pressure at outlet 18 for any particular fluid level in standpipe 13. The pressure regulator 10 is adjusted to a pressure of from 15–25 mm of mercury but a nominal pressure of 20 mm of mercury has been found to be satisfactory.

It will be understood that changes and modifications may be made to the above-described method and apparatus by those skilled in the art without departing from the spirit and scope of the invention as set forth in the claims appended hereto.

I claim:
1. Apparatus for ophthalmic surgery comprising:
   a pressure regulator of the spring-biased diaphgram type having an inlet, an outlet and a diaphragm having an upper side and a lower side;
   a supply of treatment fluid connected to said inlet of said pressure regulator;
   a first hypodermic needle connected to said outlet of said pressure regulator;
   a generally vertical bias fluid tube having a lower end communicating with the upper side of said diaphragm of said pressure regulator;
   a bias bleed means communicating with the upper side of said diaphragm of said pressure regulator for bleeding fluid from said vertical tube to reduce the pressure at said outlet at a predetermined rate; and
   pressure relief means providing an outflow path for fluid from said hypodermic needle.
2. The apparatus of claim 1 wherein said bias bleed means is a tube of predetermined length and inside diameter.
3. The apparatus of claim 2 wherein said tube has a length of from about 30 cm to 100 cm and an inside diameter of from about 0.75 mm to 1.5 mm.
4. The apparatus of claim 3 wherein said tube is about 38 cm long and has an inside diameter of about 1.5 cm.
5. The apparatus of claim 1 wherein said pressure relief means is a tube of predetermined length and diameter communicating with said first hypodermic needle.
6. The apparatus of claim 5 wherein said tube is about 50 cm long and has an inside diameter of about 0.75 mm.
7. The apparatus of claim 6 wherein said tube is about 200 cm long and has an inside diameter of about 1.5 mm.
8. The apparatus of claim 1 wherein said pressure relief means comprises a second hypodermic needle communicating with a tube of predetermined length and inside diameter.
9. The apparatus of claim 8 wherein said tube has a length of from about 50 cm to 200 cm and an inside diameter of from about 0.75 mm to 1.5 mm.
10. The apparatus of claim 9 wherein said tube is about 100 cm long and has an inside diameter of about 0.75 mm.
11. The apparatus of claim 1 wherein said pressure regulator is of the flow compensating type.

* * * * *